United States Patent [19]

Giacomoni et al.

[11] Patent Number: 5,250,290

[45] Date of Patent: Oct. 5, 1993

[54] COSMETIC USE OF A COMPOSITION HAVING ANTIERYTHEMAL ACTIVITY AND CORRESPONDING COMPOSITION

[75] Inventors: Paolo Giacomoni, Enghien-les-Bains; Jean-Luc Morançais, Ozoir-la-Ferriere; Alain Lety, Lagny, all of France

[73] Assignee: L'Oreal, Paris, France

[21] Appl. No.: 784,175

[22] Filed: Oct. 30, 1991

[30] Foreign Application Priority Data

Oct. 30, 1990 [FR] France .................. 90 13437

[51] Int. Cl.⁵ .................. A61K 7/42; A61K 7/48
[52] U.S. Cl. .................. 424/59; 424/401; 514/773
[58] Field of Search .................. 424/401, 59; 514/773

[56] References Cited

U.S. PATENT DOCUMENTS

| | | | |
|---|---|---|---|
| 4,767,741 | 8/1988 | Komar et al. | 424/401 |
| 5,063,057 | 11/1991 | Spellman et al. | 424/401 |
| 5,073,296 | 12/1991 | Kopolow et al. | 424/401 |
| 5,082,661 | 1/1992 | Melnik et al. | 424/401 |

FOREIGN PATENT DOCUMENTS

| | | | |
|---|---|---|---|
| 0256472 | 2/1988 | European Pat. Off. | 514/847 |
| 8706499 | 11/1987 | PCT Int'l Appl. | 424/401 |

OTHER PUBLICATIONS

Takeshi Okamoto, "Liposome Containing Hemoglobin and Preparation Thereof", Patent Abstracts of Japan, vol. 14, No. 453, (C-764) [4396], Sep. 1990.

Chem. Abstracts, vol. 96, No. 16, 129592F, "A mixture of placental and Yeast Extracts as an Inhibitor of Melanin", May 1981.

French Search Report for FR 90 13437, May 27, 1991.

*Primary Examiner*—Dale R. Ore
*Attorney, Agent, or Firm*—Cushman, Darby & Cushman

[57] ABSTRACT

The invention concerns the use of an active quantity of nicotinamide adenosine dinucleotide (NAD) and/or its phosphate ester (NADP) by topical application. The NAD and/or the NADP can advantageously be encapsulated in vesicles of lamellar lipidic structure. This composition is usable for the protection of the skin against solar irradiation.

19 Claims, No Drawings

COSMETIC USE OF A COMPOSITION HAVING ANTIERYTHEMAL ACTIVITY AND CORRESPONDING COMPOSITION

The invention concerns a cosmetic use by topical application of a composition having antierythemal activity and capable of protecting the skin from the harmful effects of solar radiation.

It is known that if irradiation is too prolonged or too intense, solar radiation is capable of creating on the skin an erythema which can not only be painful but can also in certain cases go as far as to the burn state. It is therefore well known to seek to protect the skin by the exogenous route to reduce the solar erythema, using a cosmetic composition applied topically, either by pre-application or by post-application in relation to the exposure to the radiation.

Antierythemal compositions are at present made by applying one or other of two general principles.

According to a first principle, the topical application of the composition enables absorbent filters for ultraviolets A and B to be placed on the skin. Unfortunately most of the chemical compounds with the filtering properties have only a limited effectiveness in the proportions in which they are generally used. Compositions are therefore obtained having higher or lower indices of protection according to the quantity of filter used.

According to a second principle, instead of setting up an external barrier, anti-inflammatory agents are used, which pass through the skin and at the cell itself reduce the erythemal effect of the ultraviolet rays. Unfortunately, the use of anti-inflammatory agents includes some disadvantages. Among the anti-inflammatory agents which can be used, three categories can be quoted:

a) in the first place, non-steroid anti-inflammatory agents, such as indomethacin and phenylbutazone. These agents, applied topically, produce powerful desquamation. If there is sufficient penetration and they pass into the general system they produce disorders of the digestive system and impairment of leucocyte growth and they interfere with some medicaments;

b) in the second place, the corticoids such as prednisone, dexamethasone or cortisone. These agents unfortunately have pleiotropic effects. They can increase the glucose content of the blood, reduce the immune response, increase the renewal of osseous tissue, and cause hydrosodic retention;

c) in the third place, the derivatives of salicylic acid. Unfortunately these agents interfere with some medicaments and slow down coagulation.

It therefore appears that at the present time the use of anti-inflammatory agents in compositions for topical application aiming at reducing at the cell the erythemal effect of ultraviolet rays can be difficult to envisage at the cosmetic level, having regard to the various disadvantages mentioned above.

The object of the present invention is to propose, in order to obtain an anti-erythemal effect, the cosmetic use of a compound which does not present the disadvantages of the anti-inflammatory agents mentioned above, notably because of the fact that it is a compound present in the cells of the epidermis in a proportion of 0.1% of the dry weight of the latter. The compound in question is nicotinamide adenosine dinucleotide, in its non-esterified form (NAD) or in its form esterified by a phosphate group (NADP).

It has already been indicated, in European Patent Application 256 472, that NAD or NADP could be used in cosmetic compositions to activate the cells of the dermis in order to obtain an improvement of the elasticity of the skin and of its softness, a reduction of wrinkles and generally an anti-aging effect on the skin. According to the invention, it has now been discovered that the exogenous application of NAD or NADP enables solar erythema to be reduced effectively without the appearance of troublesome side effects.

NAD or NADP was known to be implicated in the oxidation-reduction mechanisms which accompany several biochemical processes and, in particular, glycolysis. It has been shown that the lethal effect of ionizing radiations is due to the stopping of glycolysis and that this stopping is caused by the reduction of the quantity of intracellular NAD. It has also been shown that irradiation by an ultraviolet radiation brings about a reduction of the NAD content in the cells of the epidermis (Balard and Giacomoni, Mutation Research, 219 (1989), pages 71-79). Nevertheless, nothing allowed the specialist to imagine that the topical application of NAD or of NADP was capable of having a significant effect in favour of the reduction of erythema caused by solar radiation, whether by pre- or post-application in relation to the exposure to the said radiation.

It has also been observed according to the invention that the above-mentioned anti-erythemal effect appears whatever the nature of the vehicle of the cosmetic composition, that is to say whether it be an aqueous solution, an emulsion or an encapsulation in the lipidic vesicles of lamellar structure. It has also been observed that the anti-erythemal effect is the more marked the greater the quantity of NAD or NADP applied.

The subject matter of the present invention is consequently the cosmetic use of nicotinamide adenosine dinucleotide (NAD) and/or of nicotinamide adenosine dinucleotide phosphate (NADP) by topical application to reduce the erythema associated with solar irradiation.

It can advantageously be provided that the NAD and/or the NADP be in an aqueous solution encapsulated in the vesicles of laminar lipidic structure; in this case the vesicles can be defined by the lipidic layers obtained from ionic or nonionic lipids. Nevertheless, the vehicle of the composition can also be an aqueous solution or an emulsion.

In the use according to the invention, the NAD and/or the NADP can be applied to the skin before or after the skin's irradiation; it is preferred that this application be made at a rate of 10 to 20 mg/cm$^2$. The application can advantageously be carried out by spreading on the skin a composition containing from 0.05 to 1% by weight, and preferably from 0.2 to 1% by weight of NAD or NADP, in relation to the total weight of the composition. Preferably an aqueous solution of NAD in the non-ionic lipid vesicles is used.

The invention also has as subject matter a cosmetic composition intended for implementing the use according to the invention as defined above. Such a composition can advantageously contain, in a cosmetically acceptable medium, from 0.05 to 1% by weight of NAD or NADP in relation to the total weight of the composition; in this composition the NAD and/or the NADP can be in an aqueous solution encapsulated in the vesicles of lamellar lipidic structure, these vesicles being defined by the lipidic layers obtained from ionic or nonionic lipids. However, in this composition the vehicle of the NAD and/or of the NADP can also be an aqueous solution or an emulsion. When the NAD or NADP is encapsulated in the vesicles of lamellar lipidic structure consisting of nonionic amphiphilic lipids, the latter can advantageously be chosen from the group consisting of (1) linear or branched polyglycerol ethers of formula $$RO\mathrm{-\!\!\!+\!\!\!}C_3H_5(OH)O\mathrm{\!\!\!+\!\!\!-}_{\overline{n}}H$$

in which:

—$C_3H_5(OH)O$ is represented by the following structures taken as a mixture or separately:

$$-CH_2CHOHCH_2O-;\ -CH_2-\underset{\underset{CH_2OH}{|}}{CH}O-;\ -CH-CH_2O-;$$
(with $CH_2OH$ on the third structure)

$\overline{n}$ is a mean statistical value between 1 and 6;
R represents:
- (a) a linear or branched, saturated or unsaturated aliphatic chain, containing from 12 to 30 carbon atoms; or hydrocarbon radicals of the alcohols of lanolin;
- (b) an $R^1CO$ group, where $R^1$ is a linear or branched aliphatic $C_{11}$–$C_{17}$ radical;
- (c) an $R^2$—[—$OC_2H_3(R^3)$—]— group, where:
  $R^2$ can have the significance (a) or (b) given for R;
  —$OC_2H_3(R^3)$— is represented by the following structures, taken as a mixture or separately:

$$-\underset{R^3}{\underset{|}{O}CH}-CH_2-\ \text{and}\ -O-CH_2-\underset{R^3}{\underset{|}{CH}}-$$

where $R^3$ has the significance (a) given for R;
(2) linear or branched polyglycerol ethers having two fatty chains;
(3) polyethoxylated fatty alcohols and polyethoxylated sterols and phytosterols;
(4) polyol ethers;
(5) ethoxylated or non-ethoxylated polyol esters;
(6) glycolipids of natural or synthetic origin
(7) hydroxyamides represented by the formula:

$$R^4-CHOH-\underset{R^5-CONH}{\underset{|}{CH}}-COA$$

in which:
$R^4$ designates a $C_7$–$C_{21}$ alkyl or alkenyl radical;
$R^5$ designates a $C_7$–$C_{31}$ saturated or unsaturated hydrocarbon radical;
COA designates a group chosen from the two following groups:
a $$\underset{R^6}{\underset{|}{CON}}-B$$

group where:
B is a radical derived from mono- or polyhydroxylated primary or secondary amines; and $R^6$ designates a hydrogen atom or a methyl, ethyl or hydroxyethyl radical; and
a —COOZ group, where Z represents a $C_3$–$C_7$ polyol group.

In the case where NAD and/or NADP is (or are) encapsulated in the vesicles of lamellar lipidic structure made up from ionic lipids, the latter can advantageously be from the group consisting of the natural or synthetic phospholipids and anionic compounds.

When NAD and/or NADP are encapsulated in the vesicles as indicated above, the lipids constituting the layers of the vehicles can be associated with at least one additive from the group consisting of:
long-chain alcohols and diols;
sterols;
long-chain amines and their quaternary ammonium derivatives;
dihydroxyalkylamines; polyethoxylated fatty amines; esters of long-chain aminoalcohols; and their salts and quaternary ammonium derivatives;
phosphate esters of fatty alcohols;
alkyl sulphates
certain polypeptides and certain proteins.

A preferred composition according to the invention as defined above contains NAD encapsulated in vesicles of non-ionic amphiphilic lipids.

The examples below show the effectiveness of the compositions according to the invention in reducing solar erythema by pre- or post-application.

EXAMPLE 1

Application before irradiation (comparative)

In this example the effects of ultraviolet irradiation on guinea pigs with pre-application will be compared in the case where either a vesicular dispersion containing NAD or a control vesicular dispersion is used.

(a) Preparation of the control vesicular dispersion (composition A)

An association is prepared, in the proportions by weight of 47, 5/47 and 5/5, of three lipids, that is the nonionic lipid of formula $C_{16}H_{33}OCH_2CHOHCH_2OCH_2CHOHCH_2OH$, cholesterol, and sodium dicetylphosphate. This association of lipids is obtained by melting under nitrogen at 130° C. The association of lipids thus obtained is mixed with an equal weight of a PBS buffer and hydration is allowed to take place at 75° C. in order to obtain a lamellar phase. Then PBS buffer (5.25 times the weight of the lamellar phase) is added to this lamellar phase, the lipids are dispersed to obtain vesicles (shaking at 50° C. for 2 hours), and the dispersion is subjected to the action of ultrasound.

The dispersion thus obtained contains 8% by weight of lipids in the PBS buffer in relation to the total weight of the composition. The mean diameter of the vesicles is 206±4 nm; the size polydispersity factor is 0.31±0.02; the volume fraction of the vesicles (that is the volume occupied by the vesicles in relation to the whole dispersion) is 27%; and the encapsulation ratio of the vesicles (that is the volume encapsulated in the vesicles per unit weight of lipids) is 2.4 μl/mg.

b) Preparation of a vesicular dispersion containing NAD (composition B)

A solution of NAD in the PBS buffer is prepared at a concentration of $2\times10^{-2}M$.

A vesicular dispersion is prepared as indicated under a) by replacing the PBS buffer by the NAD solution prepared as indicated above. There is thus obtained an 8% by weight dispersion of lipids, in relation to the total weight of the composition. The mean diameter of the vesicles is 206±4 nm; the size polydispersity factor is 0.31±0.02; the volume fraction of the vesicles is 26%; and the encapsulation ratio of the vesicles is 2.2 μl/mg.

The two vesicular compositions prepared as indicated under a) and b) above were used in comparative tests on albino guinea-pigs of the Hartley strain, weighing from 350 to 400 g. The hair is removed from the back of the animals 72 hours before irradiation. The irradiation is carried out with UVB generator tubes so as to have 2 mw/cm² of UVB on the back of an irradiated animal. On each animal, two sites on each side are delimited, the right-hand side not being treated. A mask delimits the irradiated zone. The test products are applied by gentle digital massage for about 30 seconds at the rate of 0.1 ml per site (surface area treated = 7 cm²). For each series of tests a batch of 10 to 15 animals is used.

If the application had taken place after irradiation, which is not the case in this example but corresponds to Example 2, it would have been carried out just after the end of irradiation, and then 30 minutes and then 60 minutes after, that is three times.

One irradiation lasts about 1 hour 30 minutes. 3 hours 30 minutes after the start of the irradiation, the treated sites are washed with lukewarm water and wiped; 30 minutes later, the erythemas are assessed by a trained observer according to the following score:

| SCORE | ERYTHEMA |
| --- | --- |
| 0 | No erythema |
| 0.5 | Erythema only just visible |
| 1 | Erythema equal to a minimum erythemal dose (MED) |
| 2 | Definite erythema |
| 3 | Marked erythema |
| 4 | Intense erythema |

If slight oedema is visible in addition to the erythema, the score is increased by one point. The same examination with evaluation is also carried out 24 hours after the start of the irradiation.

The visual scores of the left sides are compared by a Wilcoxon test for matched series with those obtained for the right sides which are only irradiated. If the difference is significant, a percentage inhibition of erythema P is calculated as follows:

$$P = 100 \times \frac{SMD - SMG}{SMD}$$

with

SMD = mean score corresponding to the right, untreated side of the animals

SMG = mean score corresponding to the left, treated side of the animals

The results obtained have been recorded in Table I, which follows. The results corresponding to the compositions A and B, prepared as indicated at points a) and b) respectively of the present example, have been compared with the control results corresponding to an irradiation without any treatment obtained under the same conditions. It is observed that the composition B causes a significant result after 24 hours to appear, corresponding to a percentage inhibition of 38%, while the vesicular composition A, which contains neither NAD nor NADP, does not give any significant result.

TABLE I

|  | SMG | | P (%) | | Significance | |
| --- | --- | --- | --- | --- | --- | --- |
|  | 4 h | 24 h | 4 h | 24 h | 4 h | 24 h |
| Control | 3.40 | 1.88 |  |  | N.S. | S. |
| Composition B | 3.42 | 1.17 | — | 38% |  |  |
| Control | 3.58 | 1.44 |  |  | N.S. | N.S. |
| Composition A | 3.54 | 1.38 | — | — |  |  |

N.S. = not significant
S. = significant

EXAMPLE 2: Application after irradiation

A composition A consisting of a PBS buffer is prepared.

A composition B is prepared, consisting of a 2×10⁻² M solution of NAD in composition A.

A composition C is prepared as indicated for composition A of Example 1. In this case, the mean diameter of the vesicles obtained is 206±3 nm; the size polydispersity factor is 0.26±0.02; the volume fraction of the vesicles is 53%; and the encapsulation ratio of the vesicles is 5.6 μl/mg.

A composition D is prepared as indicated for the composition B of Example 1, the vesicles encapsulating the NAD. In this case, the mean diameter of the vesicles is 184±2 nm; the size polydispersity factor is 0.22±0.02; the volume fraction of the vesicles is 40%; and the encapsulation ratio of the vesicles is 4 μl/mg.

The results obtained with the compositions A, B, C, D defined above are compared with the results obtained with the untreated controls; the method of application of the compositions and the method of irradiation is that defined for Example 1; the quantification of the results is the same as that defined for Example 1. The mean scores of the treated left sides are given in Table II under the name SMG; the percentage inhibition is calculated when the results of the treatments are significant in relation to the controls. As for Example 1, the scores are recorded 4 hours and 24 hours after the start of irradiation.

According to the definitions given above, only the compositions B and D of this example are compositions according to the invention. The table shows that

TABLE II

|  | SMG | | P (%) | | Significance | |
| --- | --- | --- | --- | --- | --- | --- |
|  | 4 h | 24 h | 4 h | 24 h | 4 h | 24 h |
| Control | 2.50 | 0.77 |  |  | S. | S. |
| Composition D | 2.00 | 0.29 | 20% | 62 % |  |  |
| Control | 2.17 | 0.90 |  |  | N.S. | N.S. |
| Composition C | 2.42 | 0.69 | — | — |  |  |
| Control | 2.71 | 1.23 |  |  | N.S. | S. |
| Composition B | 2.31 | 0.73 | — | 41% |  |  |
| Control | 2.50 | 1.15 |  |  | N.S. | N.S. |
| Composition A | 2.88 | 1.46 | — | — |  |  |

N.S. = not significant
S. = significant the compositions B and D give significant results 24 hours after the irradiation, that is to say percentages inhibition of 41% and 62% respectively. Moreover the composition D gives a significant result 4 hours after the start of irradiation with a percentage inhibition of 20%. It is thus observed that the anti-erythermal effect of NAD appears whatever the vehicle, but that it is more marked when the NAD is encapsulated in the vesicles.

EXAMPLE 3

The following formulation is prepared:

| | |
|---|---|
| Nonionic amphiphilic lipid of formula $C_{16}H_{32}OCH_2CHOHCH_2OCH_2CHOHCH_2OH$ | 4.75 g |
| Cholesterol | 4.75 g |
| Sodium dicetylphosphate | 0.5 g |
| Glycerol | 4.0 g |
| Perfume | qsp |
| Preservative | qsp |
| Solution of NAD ($2 \times 10^{-2}$ M) in the PBS buffer | qsp 100 g |

The composition is prepared as in Example 1. The glycerol is introduced before the hydration of the lipidic phase. The perfume and the preservative are introduced at the time of dilution of the vesicular phase.

The composition is a skin care fluid. It is applied after exposure to the sun at the rate of 14 mg cm$^2$ immediately after exposure and then one hour and two hours after exposure. The intensity of solar erythema is notably reduced.

EXAMPLE 4

The following formulation is prepared:

| | |
|---|---|
| Nonionic amphiphilic lipid of formula $C_{16}H_{32}OCH_2CHOHCH_2OCH_2CHOHCH_2OH$ | 4.75 g |
| Cholesterol | 4.75 g |
| Sodium dicetylphosphate | 0.5 g |
| Solution of NAD ($2 \times 10^{-2}$ M) in the PBS buffer | qsp 45.0 g |

The vesicular dispersion is prepared as in Example 3. The following substances are added to this dispersion:

| | |
|---|---|
| Perfume | 0.2 g |
| Oil of Purcellin | 25.0 g |
| Mixture of carboxyvinyl acids marketed under the name "Carbopol 940" | 0.2 g |
| Triethanolamine | 0.2 g |
| Solution of NAD ($2 \times 10^{-2}$ M) in the PBS buffer | qsp 15.0 g |

This skin care cream is applied as in Example 3, and gives the same results.

EXAMPLE 5

The following formulation is prepared:

| | |
|---|---|
| Glyceryl stearate | 2 g |
| Tween 60 (20-moles ethoxylate of sorbitan monostearate) | 1 g |
| Cetyl alcohol | 0.5 g |
| Stearic acid | 1 g |
| Carbopol 940 | 0.2 g |
| Perhydrosqualene | 15 g |
| Liquid fraction of karite nut butter | 10 g |
| Perfume | 0.1 g |
| Solution of NAD ($2 \times 10^{-2}$ M) in PBS | qsp 100 g |

This skin care cream is applied as in Example 3, and gives the same results.

We claim:

1. A composition for protecting the skin from the harmful effects of solar radiation comprising, in a cosmetically acceptable medium, an aqueous solution of a compound having anti-erythemal activity and being selected from the group consisting of nicotinamide adenosine dinucleotide, nicotinamide adenosine dinucleotide phosphate and a mixture thereof, said aqueous solution being encapsulate in vesicles of an ionic or nonionic amphiphilic lipid, said vesicles having a lamellar structure and said compound having anti-erythemal activity being present in an amount effective to protect the skin from the harmful effects of solar radiation.

2. The composition of claim 1 wherein said lipid vesicles are nonionic amphiphilic lipid vesicles.

3. The composition of claim 1 wherein said aqueous solution is a solution of nicotinamide adenosine dinucleotide encapsulated in nonionic amphiphilic lipid vesicles.

4. The composition of claim 1 wherein said lipid vesicles are ionic amphiphilic lipid vesicles.

5. The composition of claim 1 wherein said nonionic amphiphilic lipid is selected from the group consisting of (1) a linear or branched polyglycerol ether having the formula $$RO + C_3H_5(OH)O \frac{1}{n} H$$

wherein $-C_3H_5(OH)O$ represents, separately or in admixture, $$-CH_2CHOHCH_2O-, \quad -CH_2-CHO- \atop \phantom{-CH_2-}CH_2OH \quad \text{and} \quad -CH-CH_2O-; \atop \phantom{-CH-}CH_2OH$$

$\overline{n}$ has a mean statistical value ranging from 1 to 6;

R represents (a) a linear or branched, saturated or unsaturated aliphatic chain containing from 12 to 30 carbon atoms or a hydrocarbon radical of lanolin alcohols, (b) $R^1CO$ wherein $R^1$ is a linear or branched aliphatic $C_{11}$–$C_{17}$ radical, or (c)

$$R^2 + OC_2H_3(R^3) +$$

wherein $R^2$ has the meaning (a) or (b) above for R and $-OC_2H_3(R^3)$ represents, separately or in admixture $$-OCH-CH_2- \atop \phantom{-O}R^3 \quad \text{and} \quad -O-CH_2-CH- \atop \phantom{-O-CH_2-}R^3$$

wherein $R^3$ has the meaning (a) above for R;

(2) a linear or branched polyglycerol ether having two fatty chains;

(3) a polyethoxylated fatty alcohol, a polyethoxylated sterol or phytosterol;

(4) a polyether;

(5) an ethoxylated or non-ethoxylated polyol ester;

(6) a glycolipid of natural or synthetic origin; or (7) a hydroxyamide having the formula $$R^4-CHOH-CH-COA \atop R^5CONH$$

wherein $R^4$ represents an alkyl or alkenyl radical having 7 to 21 carbon atoms, $R^5$ represents a saturated or unsaturated hydrocarbon radical having 7–31 carbon atoms, and COA represents (a)

$$-CON-B$$
$$\phantom{-CON}|$$
$$\phantom{-CON-}R^6$$

wherein B is a radical derived from a mono- or polyhydroxylated primary or secondary amine and $R^6$ represents hydrogen, methyl, ethyl or hydroxyethyl, or (b) —COOZ wherein Z represents a $C_3$–$C_7$ polyol group.

6. The composition of claim 1 wherein said ionic amphiphilic lipid is a natural or synthetic phospholipid or an anionic compound.

7. The composition of claim 1 wherein the lipid constituent of said vesicles is combined with at least one additive selected from the group consisting of (1) a long chain alcohol or diol;
(2) a sterol;
(3) a long chain amine or a quaternary ammonium derivative thereof;
(4) a dihydroxyalkylamine, or a salt or a quaternary ammonium derivative thereof;
(5) a polyethoxylated fatty amine, or a salt or a quaternary ammonium derivative thereof;
(6) an ester of a long chain amino alcohol, or a salt or a quaternary ammonium derivative thereof;
(7) a phosphate ester of a fatty alcohol;
(8) an alkyl sulphate;
(9) a polypeptide; and
(10) a protein.

8. The composition of claim 1 wherein said compound having anti-erythemal activity is present in an amount ranging from 0.05 to 1 percent by weight based on the total weight of said composition.

9. The composition of claim 1 wherein said compound having anti-erythemal activity is present in an amount ranging from 0.2 to 1 percent by weight based on the total weight of said composition.

10. A process for protecting the skin from the harmful effects of solar radiation comprising topically applying to the skin a composition comprising, in a cosmetically acceptable medium, an aqueous solution of a compound having anti-erythemal activity and being selected from the group consisting of nicotinamide adenosine dinucleotide, nicotinamide adenosine dinucleotide phosphate and a mixture thereof, said aqueous solution being encapsulated in vesicles of an ionic or nonionic amphiphilic lipid, said vesicles having a lamellar structure, said compound having anti-erythemal activity being present in an amount effective to protect the skin from the harmful effects of solar radiation.

11. The process of claim 10 wherein said lipid vesicles are nonionic amphiphilic lipid vesicles.

12. The process of claim 10 wherein said aqueous solution is a solution of nicotinamide adenosine dinucleotide encapsulated in nonionic amphiphilic lipid vesicles.

13. The process of claim 10 wherein said lipid vesicles are ionic amphiphilic lipid vesicles.

14. The process of claim 10 wherein said nonionic amphiphilic lipid is selected from the group consisting of (1) a linear or branched polyglycerol ether having the formula $$RO+C_3H_5(OH)O+_{\overline{n}}H$$

wherein

—$C_3H_5(OH)O$ represents, separately or in admixture, $$-CH_2CHOHCH_2O-, \quad -CH_2-CHO- \text{ and } -CH-CH_2O-;$$
$$\phantom{-CH_2CHOHCH_2O-,\ -CH_2-}|\phantom{CHO- \text{ and } -CH-}|$$
$$\phantom{-CH_2CHOHCH_2O-,\ -CH_2-}CH_2OH\phantom{\text{ and } -CH-}CH_2OH$$

$\overline{n}$ has a mean statistical value ranging from 1 to 6;

R represents (a) a linear or branched, saturated or unsaturated aliphatic chain containing from 12 to 30 carbon atoms or a hydrocarbon radical of lanolin alcohols, (b) $R^1CO$ wherein $R^1$ is a linear or branched aliphatic $C_{11}$–$C_{17}$ radical, or (c)

$$R^2+OC_2H_3(R^3)+$$

wherein $R^2$ has the meaning (a) or (b) above for R and —$OC_2H_3(R^3)$ represents, separately or in admixture $$-OCH-CH_2- \text{ and } -O-CH_2-CH-$$
$$\phantom{-O}|\phantom{CH-CH_2- \text{ and } -O-CH_2-C}|$$
$$\phantom{-O}R^3\phantom{CH-CH_2- \text{ and } -O-CH_2-C}R^3$$

wherein $R^3$ has the meaning (a) above for R;

(2) a linear or branched polyglycerol ether having two fatty chains;

(3) a polyethoxylated fatty alcohol, a polyethoxylated sterol or phytosterol;

(4) a polyether;

(5) an ethoxylated or non-ethoxylated polyol ester;

(6) a glycolipid of natural or synthetic origin; or (7) a hydroxyamide having the formula $$R^4-CHOH-CH-COA$$
$$\phantom{R^4-CHOH-CH}|$$
$$\phantom{R^4-CHOH-}R^5CONH$$

wherein $R^4$ represents an alkyl or alkenyl radical having 7 to 21 carbon atoms, $R^5$ represents a saturated or unsaturated hydrocarbon radical having 7–31 carbon atoms, and COA represents (a)

$$-CON-B$$
$$\phantom{-CON}|$$
$$\phantom{-CON-}R^6$$

wherein B is a radical derived from a mono- or polyhydroxylated primary or secondary amine and $R^6$ represents hydrogen, methyl, ethyl or hydroxyethyl, or (b) —COOZ wherein Z represents a $C_3$–$C_7$ polyol group.

15. The process of claim 10 wherein said ionic amphiphilic lipid is a natural or synthetic phospholipid or an anionic compound.

16. The process of claim 10 wherein the lipid constituent of said vesicles is combined with at least one additive selected from the group consisting of
   (1) a long chain alcohol or diol;
   (2) a sterol;
   (3) a long chain amine or a quaternary ammonium derivative thereof;
   (4) a dihydroxyalkylamine, or a salt or a quaternary ammonium derivative thereof;
   (5) a polyethoxylated fatty amine, or a salt or a quaternary ammonium derivative thereof;
   (6) an ester of a long chain amino alcohol, or a salt or a quaternary ammonium derivative thereof;
   (7) a phosphate ester of a fatty alcohol;
   (8) an alkyl sulphate;
   (9) a polypeptide; and
   (10) a protein.

17. The process of claim 10 wherein said compound having anti-erythemal activity is present in an amount ranging from 0.05 to 1 percent by weight based on the total weight of said composition.

18. The process of claim 10 wherein said compound having anti-erythemal activity is present in an amount ranging from 0.2 to 1 percent by weight based on the total weight of said composition.

19. The process of claim 10 wherein said composition is applied to the skin at a rate of 10 to 20 mg/cm$^2$ of skin.

* * * * *